United States Patent
Strong et al.

(10) Patent No.: US 10,418,605 B2
(45) Date of Patent: Sep. 17, 2019

(54) EMBEDDED FORMATION OF WEARABLE AND FLEXIBLE BATTERIES

(71) Applicant: INTEL CORPORATION, Santa Clara, CA (US)

(72) Inventors: Veronica A. Strong, Chandler, AZ (US); Sasha N. Oster, Chandler, AZ (US); Feras Eid, Chandler, AZ (US); Aranzazu Maestre Caro, Hillsboro, OR (US)

(73) Assignee: Intel Corporation, Santa Clara, CA (US)

( * ) Notice: Subject to any disclaimer, the term of this patent is extended or adjusted under 35 U.S.C. 154(b) by 130 days.

(21) Appl. No.: 15/475,751

(22) Filed: Mar. 31, 2017

(65) Prior Publication Data

US 2018/0287115 A1 Oct. 4, 2018

(51) Int. Cl.
*H01M 2/10* (2006.01)
*H01M 4/04* (2006.01)
*C23C 18/38* (2006.01)
*C23C 18/16* (2006.01)
*B32B 5/24* (2006.01)
*G06F 1/16* (2006.01)
*H01L 23/538* (2006.01)
*C23C 18/20* (2006.01)
*C23C 18/30* (2006.01)
(Continued)

(52) U.S. Cl.
CPC ............. *H01M 2/1066* (2013.01); *B32B 5/24* (2013.01); *C23C 18/1641* (2013.01); *C23C 18/2086* (2013.01); *C23C 18/30* (2013.01); *C23C 18/38* (2013.01); *G06F 1/163* (2013.01); *H01L 23/5387* (2013.01); *H01M 4/0402* (2013.01); *H01M 4/661* (2013.01); *H01M 10/0422* (2013.01); *H01M 10/0436* (2013.01); *A41D 1/002* (2013.01); *A61B 5/01* (2013.01); *A61B 5/024* (2013.01); *A61B 5/14532* (2013.01); *A61B 5/4266* (2013.01); *A61B 5/6804* (2013.01); *H01M 2220/30* (2013.01); *H05K 1/038* (2013.01); *H05K 2201/10037* (2013.01)

(58) Field of Classification Search
CPC .... H01M 2/1066; H01M 4/0402; H01M 4/66; H01M 4/70; H01M 4/747; H01M 2220/30; H01M 10/0422; H01M 10/0436; H01M 4/661; H05K 1/038; H05K 2201/10037; A61B 5/6804; A61B 5/01; A61B 5/024; A61B 5/14532; A61B 5/4266; B32B 5/24; G06F 1/163; A41D 1/002; H01L 23/5387; C23C 18/1641; C23C 18/2086; C23C 18/30; C23C 18/38
See application file for complete search history.

(56) References Cited

U.S. PATENT DOCUMENTS 6,528,204 B1 * 3/2003 Hikmet .................. H01M 4/13
429/128
7,862,927 B2 * 1/2011 Krasnov ............. H01M 4/0426
204/192.15
(Continued)

*Primary Examiner* — Gregg Cantelmo
(74) *Attorney, Agent, or Firm* — Green, Howard & Mughal LLP

(57) ABSTRACT

An apparatus system is provided which comprises: a fabric; a self-assembled monolayer (SAM) material formed on the fabric; and a battery cell formed on the fabric, wherein a current collector of the battery cell is at least in part formed on the SAM material.

23 Claims, 12 Drawing Sheets

(51) Int. Cl.
   *H01M 4/66*     (2006.01)
   *H01M 10/04*    (2006.01)
   *A41D 1/00*     (2018.01)
   *A61B 5/00*     (2006.01)
   *H05K 1/03*     (2006.01)
   *A61B 5/01*     (2006.01)
   *A61B 5/024*    (2006.01)
   *A61B 5/145*    (2006.01)

(56) References Cited

U.S. PATENT DOCUMENTS

2006/0216589 A1* 9/2006 Krasnov ............. H01M 2/0404
                                                    429/175
2010/0261071 A1* 10/2010 Lopatin ................ H01M 4/133
                                                    429/345
2013/0224551 A1* 8/2013 Hiralal ..................... H01G 9/10
                                                    429/127
2014/0180624 A1* 6/2014 Nikonov .................. G01K 7/16
                                                    702/130
2016/0181615 A1* 6/2016 Van Duren ........... H01M 4/621
                                                    429/232

* cited by examiner

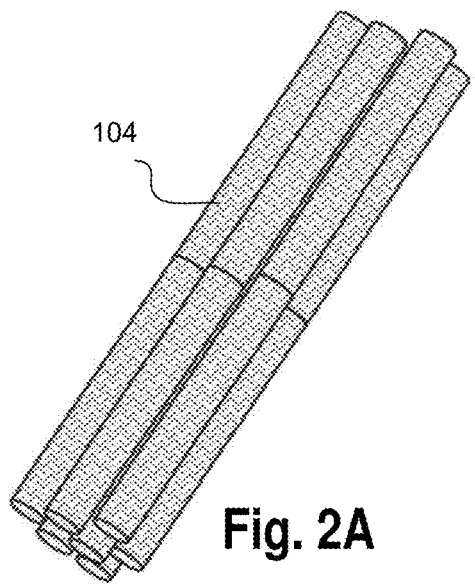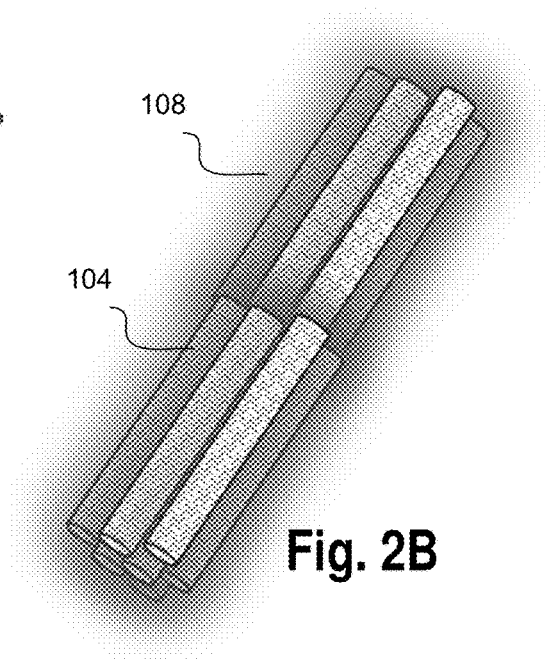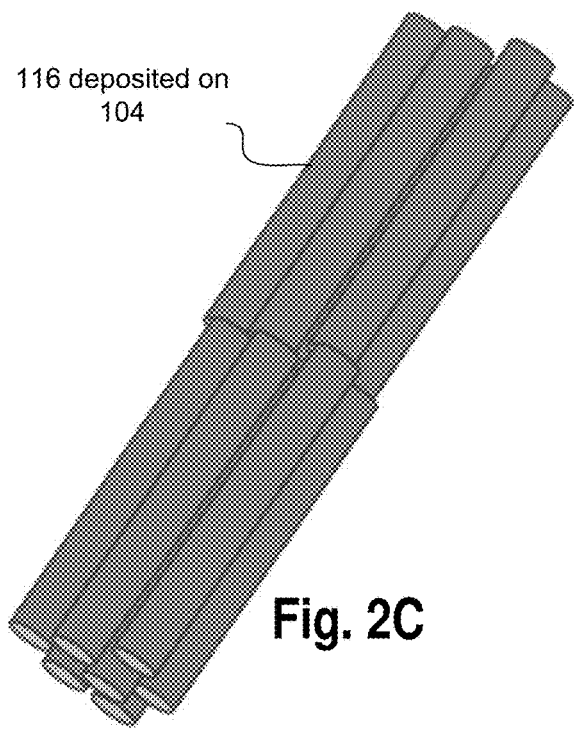

EMBEDDED FORMATION OF WEARABLE AND FLEXIBLE BATTERIES

BACKGROUND

Wearable technology is a relatively new market that has shown immense potential and has already impacted several business sectors, including health, communication, fashion, energy, and textiles. A variety of wearable devices are now being available. For example, wearable devices may use some form of textile. Smart apparel, for example, is an integration between textiles and wearable technology. Smart apparels may aim to monitor, for example, one or more parameters of the body such as body temperature, and are an area where the need to provide a light weight, thin, and flexible power source is important.

BRIEF DESCRIPTION OF THE DRAWINGS

The embodiments of the disclosure will be understood more fully from the detailed description given below and from the accompanying drawings of various embodiments of the disclosure, which, however, should not be taken to limit the disclosure to the specific embodiments, but are for explanation and understanding only.

FIGS. 2A-2G schematically illustrate formation of embedded batteries at a fiber level, according to some embodiments.

DETAILED DESCRIPTION

Figure 1A:
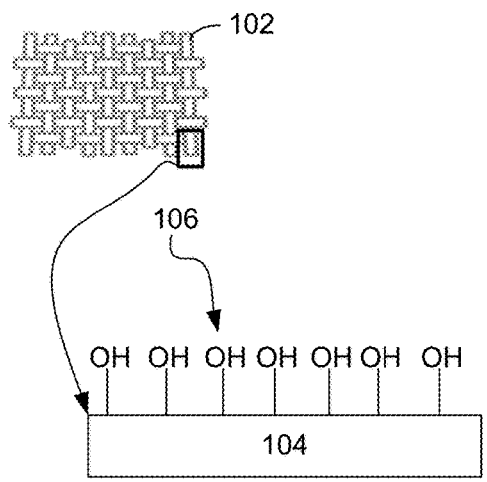
FIGS. 1A-1D schematically illustrate formation of a metal layer on a fabric, where the metal layer is subsequently used for forming embedded batteries on the fabric, according to some embodiments.

In some embodiments, one or more battery cells may be formed on a fabric of a smart apparel or a smart wearable device. For example, the fabric may have functional groups (e.g., hydroxyl groups) inherently present thereon or deposited thereon, and a self-assembled monolayer (SAM) may be formed on the fabric, e.g., by attaching the SAM to the functional groups on the fabric. Subsequently, a thin metal layer may be grown or deposited on the SAM by a deposition process such as electro-less metal plating. For example, the SAM material may serve to provide anchor points while growing the metal. A catalyst layer may facilitate formation of the metal layer on the SAM of the fabric.

In some embodiments, the metal layer may act as a current collector (e.g., a cathode current collector) of a battery cell. Subsequently, cathode material, anode material, a separation layer separating the cathode and anode material, and an encapsulant may be formed on the metal layer, thereby forming a battery cell.

The battery cell may be formed at a fiber level (e.g., while the fiber has not yet been used to form the fabric) or at a fabric level (e.g., after the fibers are woven together to form the fabric). In some embodiments, multiple battery cells may be formed adjacent to each other, and the battery cells may be configured in a serial configuration, or a parallel configuration. Varying geometry and form factors of the battery cells may be possible.

There are several technical advantages of various embodiments. For example, a SAM may facilitate good adhesion between the fabric and the metal layer of the battery. In some embodiments, a very thin stack of a battery cell may be architecturally designed by taking advantage of the thin nature of the SAM layer (e.g., a few nanometers), which may allow for the additional deposition of the thin layer of metal (e.g., which can be used as current collector). In some embodiments, the battery may be formed on a pre-woven textile or synthetic textile. In some other embodiments, the battery may be at least in part formed on the thread or fiber level and be subsequently woven into any desired textile, or may be co-woven with more traditional textiles materials to achieve a certain look or feel.

In some embodiments, the battery may be formed on a material that is commonly used with textiles, such as polyurethane sheets (e.g., thermoplastic polyurethane (TPU)). In some embodiments, polyurethane sheets or TPUs may be used to provide waterproofing for fabrics and then bonded or laminated to the textile. In an example, once the battery is formed on polyurethane sheets, the polyurethane sheets (with the batteries formed thereon) may be attached (e.g., by a lamination process) to another fabric.

In an example, by taking advantage of the large real estate area found on the fabric of, for example, an apparel, a power storage system with high battery capacity can be formed. Other technical effects will be evident from the various embodiments and figures.

In the following description, numerous details are discussed to provide a more thorough explanation of embodiments of the present disclosure. It will be apparent, however, to one skilled in the art, that embodiments of the present disclosure may be practiced without these specific details. In other instances, well-known structures and devices are shown in block diagram form, rather than in detail, in order to avoid obscuring embodiments of the present disclosure.

Note that in the corresponding drawings of the embodiments, signals are represented with lines. Some lines may be thicker, to indicate more constituent signal paths, and/or have arrows at one or more ends, to indicate primary information flow direction. Such indications are not intended to be limiting. Rather, the lines are used in connection with one or more exemplary embodiments to facilitate easier understanding of a circuit or a logical unit. Any represented signal, as dictated by design needs or preferences, may actually comprise one or more signals that may travel in either direction and may be implemented with any suitable type of signal scheme.

Throughout the specification, and in the claims, the term "connected" means a direct connection, such as electrical, mechanical, or magnetic connection between the things that are connected, without any intermediary devices. The term "coupled" means a direct or indirect connection, such as a direct electrical, mechanical, or magnetic connection between the things that are connected or an indirect connection, through one or more passive or active intermediary devices. The term "circuit" or "module" may refer to one or more passive and/or active components that are arranged to cooperate with one another to provide a desired function. The term "signal" may refer to at least one current signal, voltage signal, magnetic signal, or data/clock signal. The meaning of "a," "an," and "the" include plural references. The meaning of "in" includes "in" and "on." The terms "substantially," "close," "approximately," "near," and "about," generally refer to being within +/−10% of a target value.

Unless otherwise specified the use of the ordinal adjectives "first," "second," and "third," etc., to describe a common object, merely indicate that different instances of like objects are being referred to, and are not intended to imply that the objects so described must be in a given sequence, either temporally, spatially, in ranking or in any other manner.

For the purposes of the present disclosure, phrases "A and/or B" and "A or B" mean (A), (B), or (A and B). For the purposes of the present disclosure, the phrase "A, B, and/or C" means (A), (B), (C), (A and B), (A and C), (B and C), or (A, B and C). The terms "left," "right," "front," "back," "top," "bottom," "over," "undet," and the like in the description and in the claims, if any, are used for descriptive purposes and not necessarily for describing permanent relative positions.

FIGS. 1A-1D schematically illustrate formation of a metal layer on a fabric, where the metal layer is subsequently used for forming embedded batteries on the fabric, according to some embodiments. Referring to FIG. 1A, illustrated is a fabric 102. The fabric 102 may form, for example, a part of a wearable device, e.g., a smart apparel. The smart apparel may, for example, perform various tasks, such as measure heart rate, body temperature, perspiration, glucose levels, and/or one or more other body parameters, aid in movement of a body part, and/or the like. The fabric 102 may comprise any appropriate material, e.g., cotton, cellulose, etc. A section of a thread or a fiber 104 of the fabric 102 is also illustrated in FIG. 1A. For example, the fiber 104 represents a single fiber or thread of the fabric 102, or a group of fibers or threads bundled together.

In some embodiments, functional groups 106 may form on the fiber 104. The functional groups 106 may be inherently present on the fiber 104, or may be formed or deposited on the fiber 104. Examples of such functional groups 106 may be carboxyls, amines, thiols, hydroxyls, or any functional group that may chemically and/or physically interact with an incoming SAM. The illustration of the functional groups 106 in FIG. 1A is for illustrative purposes only, and does not reflect a manner in which the functional groups 106 are actually laid upon the fiber 104.

Figure 1B:
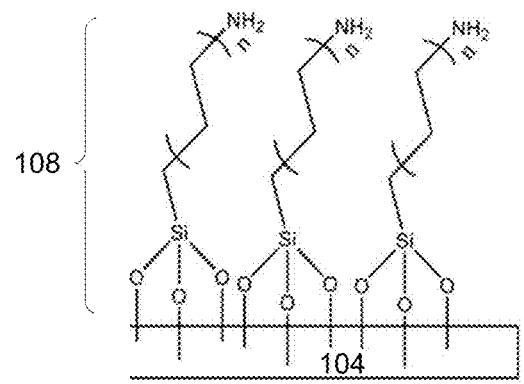

Referring now to FIG. 1B, a self-assembled monolayer (SAM) 108 may be formed on the fiber 104. In some embodiments, the SAM 108 may be formed by directly functionalizing the surface of the fiber 104. For example, the SAM 108 may be deposited by utilizing the hydroxyl groups 106 as active sites and anchor points for molecules of the SAM 108 to chemically adhere to. In some embodiments, the SAM 108 may be deposited or chemisorb through spray, dip coating, exposing the fabric to a solution or vapor, and/or another appropriate process. In some embodiments, depending on fabric surface functionality, the SAM 108 deposition process may be followed by some light heating, e.g., to ensure chemisorption.

Self-assembled monolayers may be chosen, for example, for their spontaneous ability to self-organize into a single monolayer on almost any active surface. SAMs generally may have the following chemical configuration, which may lend to their self-assembling properties: head group, an organic tail, and terminating group. SAMs may be selected based on the corresponding head group's affinity to a substrate. For example, ideally the head group may have a stronger affinity to the substrate than the terminating group. This may, for example, ensure that the SAM organizes with the head group physically and/or chemically attached to the substrate (where, in FIG. 1B, the substrate may be the fiber 104). In an example, the tail and terminating group may stick far away from the substrate surface. Thus, a SAM may be organized in a way that terminating groups may be available for further functionalization and/or chemical modification. Selecting a SAM group for the embodiment proposed here may depend on an affinity between head group and functional group on the substrate, and the final terminal group, which may play a role on the types of metals that may grow on the surface.

In some embodiments, any appropriate type of SAM material may be used as a SAM layer 108. FIG. 1B illustrates using amine group (—NH2). In some other embodiments, another type of SAM material may be used, e.g., thiol (—SH), carboxylic acid (—COOH), Pyridyl, etc.

In some embodiments, the SAM 108 may be a relatively thin layer. For example, the SAM 108 may be in the range of about 0.5 nanometer (nm) to about 2.5 nm, e.g., depending on a chain length (e.g., on a specific carbon chain length) selected for the SAM 108.

Figure 1C:
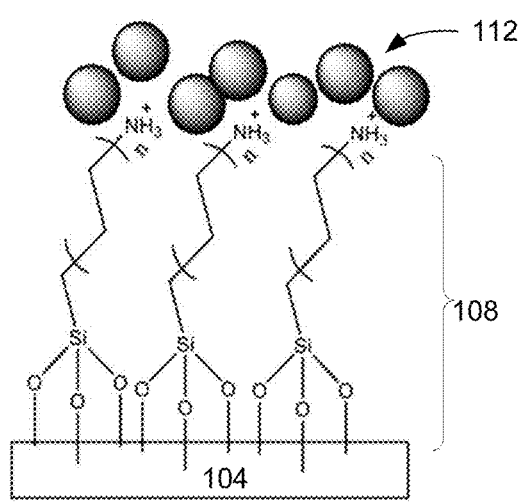
Figure 1D:
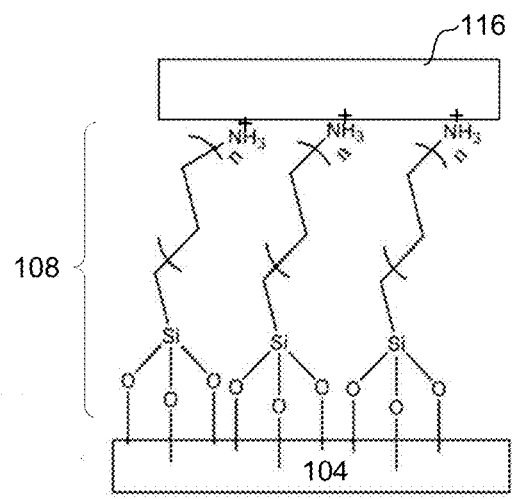

Referring now to FIG. 1C, once the SAM 108 is firmly established onto the fabric surface, catalysts 112 may be deposited on the SAM 108. For example, the catalysts 112 may comprise appropriate metal catalysts deposited and adhered by functional groups having an affinity to those catalysts. In some embodiments, the catalysts 112 may subsequently serve as anchor points for electro-less deposition of metal (e.g., Cu), as illustrated in FIG. 1D. In some embodiments, palladium catalyst ($Pd^{2+}$) may be used (e.g., when the subsequent electro-less growth of FIG. 1D is of copper), but any other suitable catalyst for selective metal growth may also be used. In an example, the palladium catalyst may be in an ionic state when deposited. In some embodiments, the catalysts 112 may be deposited by spray, dip coating, exposing the fabric to a solution or vapor, and/or another appropriate process.

Referring now to FIG. 1D, a metal layer 116 may be formed on the SAM 108. The metal layer 116 may be formed by using a deposition process such as, for example, electro-less metal plating. The catalysts 112 may subsequently serve as the anchor points for the electro-less deposition of the metal layer 116. In some embodiments, copper (Cu) may be used for the metal layer 116, although another appropriate type of metal may also be used.

In some embodiments, batteries may be formed on a fabric either at a fiber or a fabric level. For example, a fabric may comprise hundreds, thousands, or even millions of fibers. Individual thread or fiber in a fabric may comprise a bundle of tinier threads or fibers. In some embodiments, a small battery may be formed on a fiber, e.g., prior to the fiber being used to form a fabric, which is referred to herein as formation of a battery at the fiber level. In some other embodiments, a battery may be formed on a fabric (e.g., subsequent to multiple fibers being woven to form the fabric), which is referred to herein as formation of battery at the fabric level. FIGS. 2A-2G schematically illustrate formation of embedded batteries at a fiber level, according to some embodiments; and FIGS. 3A-3J schematically illustrate formation of embedded batteries at a fabric level, according to some embodiments.

Figure 2D:
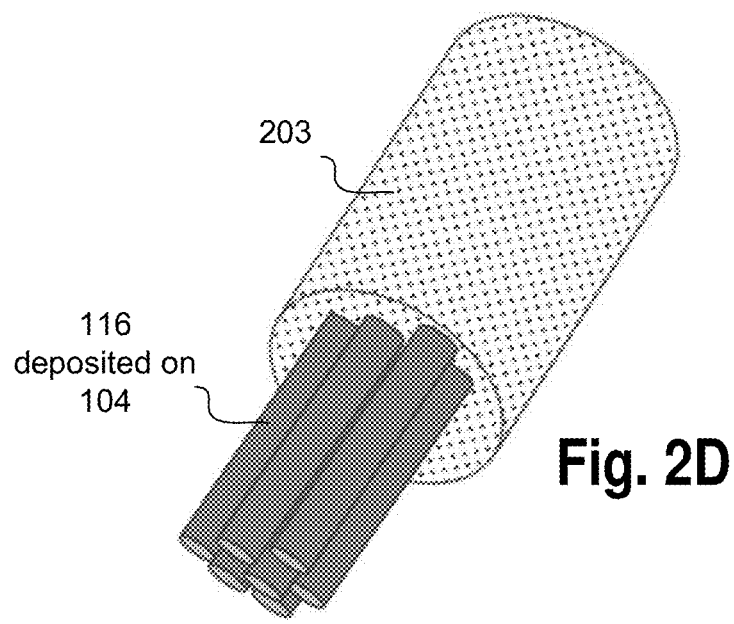

Referring to FIGS. 2A-2G, these figures illustrate formation of embedded batteries at the fiber level, e.g., prior to the fibers being woven to form a fabric. Referring to FIG. 2A, illustrated is the fiber 104 of FIGS. 1A-1D. For example, the fiber 104 in FIG. 2A is to be later used to form the fabric. As illustrated, the fiber 104 may be a bundle of smaller fibers or threads. Although the functional groups 106 of FIG. 1A may be formed on the fiber 104 of FIG. 2A, such functional groups are not illustrated in FIG. 2A.

Referring now to FIG. 2B, illustrated is the fiber 104 with the SAM 108 deposited thereon, e.g., as discussed with respect to FIG. 1B. Deposition of the SAM 108 is discussed in further details with respect to FIG. 1B. Although the catalysts 112 may be deposited on the SAM 108, the deposition of the catalysts 112 is not illustrated in FIG. 2B. In some embodiments, the SAM 108 may be a relatively thin layer. For example, the SAM 108 may be in the range of about 0.5 nanometer (nm) to about 2.5 nm, e.g., depending on a chain length (e.g., on a specific carbon chain length) selected for the SAM 108.

Referring now to FIG. 2C, illustrated is the fiber 104 with the SAM 108 deposited and the metal layer 116 deposited thereon. Deposition of the metal layer 116 on a fiber is discussed in further details with respect to FIG. 1D. In FIG. 2C, the metal layer 116 is visible, and not the pristine fiber 104. In some embodiments, the metal layer 116 may serve as a current collector for an embedded battery formed on the fiber 104.

Referring now to FIG. 2D, anode material may be deposited on the metal layer 116 to form an anode layer 203. The anode material may be deposited by printing (e.g., screen printing, ink-jet printing, etc.), spray coating, dip coating, and/or another appropriate process. Although the anode layer 203 is illustrated to cover only a section of the fiber 104, the anode layer 203 may cover the entire fiber, other sections of the fiber, and/or other sections of the fabric as well. In some embodiments, the metal layer 116 may serve as a current collector for the anode layer 203.

Figure 2E:
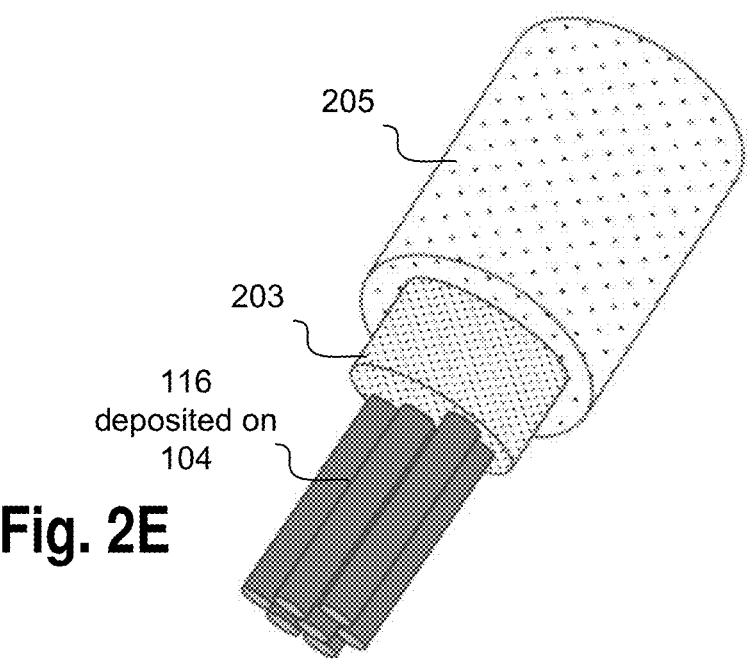

Referring now to FIG. 2E, electrolyte material, gel electrolyte material, and/or the like may be deposited on the surface of the anode layer 203 to form a separation layer 205. In some embodiments, the separation layer 205 may act as a separator between the anode and the cathode of the battery to be formed. In some embodiments, the separation layer 205 may be deposited using, for example, screen printing, exposing the fabric to vapor phase or liquid, spray coating, and/or the like.

Figure 2F:
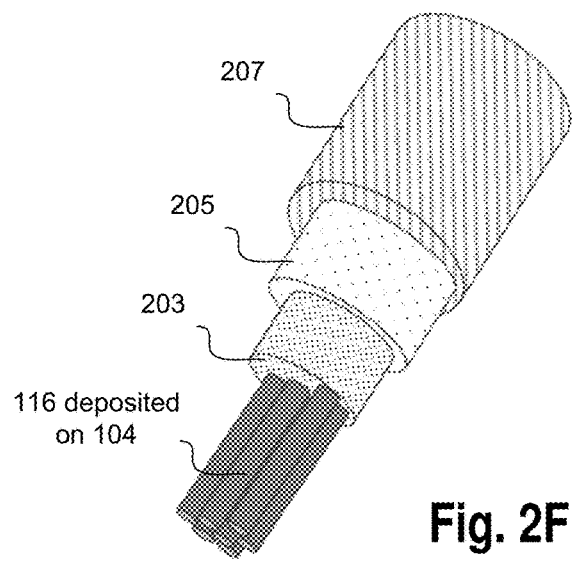

Referring now to FIG. 2F, cathode material may be deposited on the separation layer 205 to form a cathode layer 207 on top of the separation layer 205. The cathode material may be deposited by printing, spray coating, dip coating, and/or another appropriate process. Although the cathode layer 207 is illustrated to cover only a section of the fiber or fabric, the cathode layer 207 may cover all or other sections of the fiber or fabric as well.

Figure 2G:
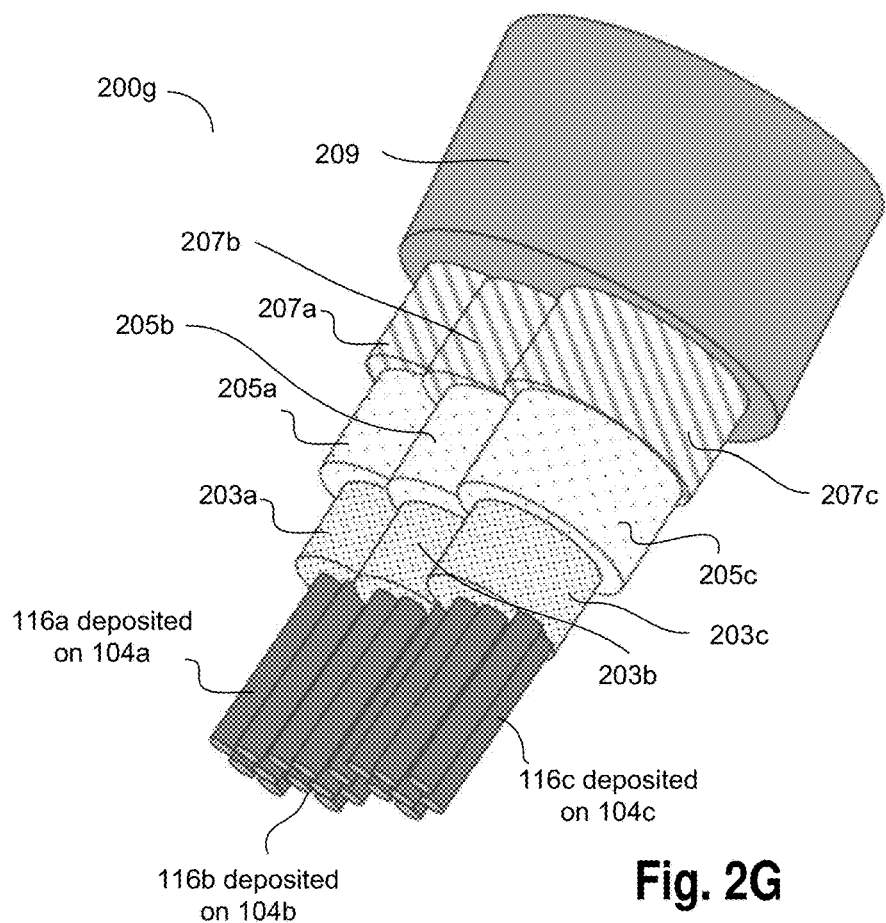

Referring now to FIG. 2G, illustrated is a component 200g. In FIGS. 2A-2F, only a single fiber 104 is illustrated. However, in FIG. 2G, three strands of fibers 104a, 104b, and 104c are illustrated, each being developed as discussed with respect to FIGS. 2A-2F. For example, the fiber 104a comprises metal layer 116a deposited thereon, an anode layer 203a, a separation layer 205a, and a cathode layer 207a formed thereon. In some embodiments, in the component 200g, a current collector layer 209 may be formed, where the current collector layer 209 may surround the three fibers 104a, 104b, and 104c. In some embodiments, the current collector layer 209 may comprise appropriate metal, e.g., copper, aluminum, etc. The current collector layer 209 may be formed by, for example, printing, sputtering, plating, and/or another appropriate metal deposition process. In some embodiments, the current collector layer 209 may act as a current collector for the cathode layers 207a, 207b, and 207c.

Although FIG. 2G illustrates three sets of fibers surrounded by the current collector layer 209, in some embodiments, one, two, four, or higher sets of fibers may be surrounded by the current collector layer. The component 200g may act as a basic battery cell, although some other process may be performed prior to using the component 200g as a battery (e.g., the final battery or set of batteries may require encapsulation). In some embodiments, subsequent to the formation of the battery, the fibers 104a, 104b, and 104c, along with the embedded batteries, may be used to form a fabric. For example, the fibers 104a, 104b, 104c may be subsequently woven into any desired textile, or may be co-woven with more traditional textiles materials to achieve a certain look or feel of the resultant fabric.

FIGS. 3A-3J schematically illustrate formation of embedded batteries at a fabric level, according to some embodiments. For example, the operations discussed with respect to these figures may be performed after the fabric is woven using multiple fibers.

It is to be noted that in some of FIGS. 3A-3J (e.g., in FIGS. 3C-3F), some of the layers in various figures may not be visually separable (e.g., may look alike), e.g., due to the limitations in the shadings and/or colors used to generate these figures. However, these illustrative limitations of the figures do not imply that the layers in the various figures are the same. The written specification discusses in details formation of the layers, and the labels used in these figures also indicate formation of the various layers.

Figure 3A:
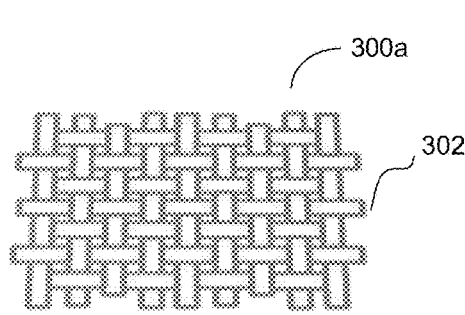
FIGS. 3A-3J schematically illustrate formation of embedded batteries at a fabric level, according to some embodiments.

Referring now to FIG. 3A, illustrated is a component 300a comprising a fabric 302. The fabric 302 may be pristine fabric, and may comprise cotton, cellulose, and/or the like.

Figure 3B:
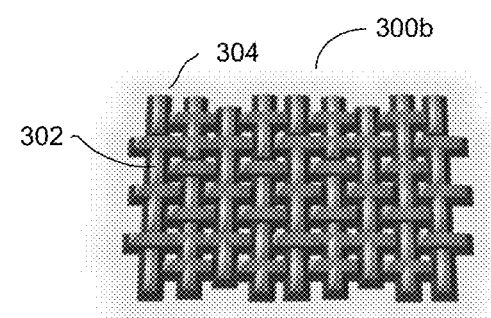

Referring now to FIG. 3B, illustrated is a component 300b comprising SAM 304 deposited on the fabric 302. Deposition of a SAM on a fabric (or a fiber of a fabric) has been discussed with respect to FIGS. 1B and 2B, and hence is not discussed in further detail herein. In some embodiments, the SAM 304 may be a relatively thin layer. For example, the SAM 304 may be in the range of about 0.5 nanometer (nm) to about 2.5 nm, e.g., depending on a chain length (e.g., on a specific carbon chain length) selected for the SAM 304.

Figure 3C:
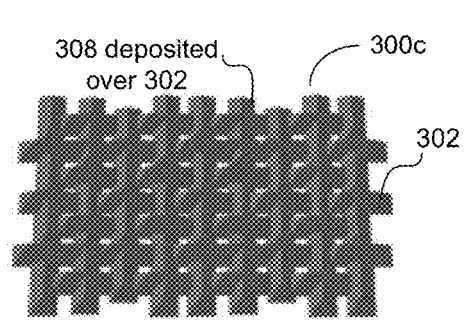

Referring now to FIG. 3C, illustrated is a component 300c comprising the fabric 302, and metal layer 308 formed thereon. Formation of a metal layer (e.g., copper layer) on a fabric (or a fiber of a fabric) has been discussed in details with respect to FIGS. 1D and 2C. In some embodiments and although not illustrated in FIG. 3C, a catalyst layer may be formed prior to the deposition of the metal layer 308, e.g., as discussed with respect to FIG. 1C.

Figure 3D:
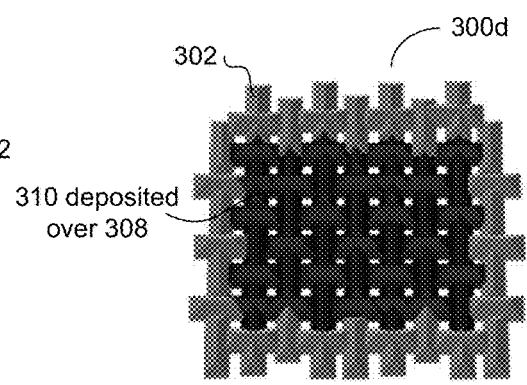

Referring now to FIG. 3D, illustrated is a component 300d comprising the fabric 302, where, in some embodiments, a cathode layer 310 may be deposited on the metal layer 308 of the fabric 302. It is to be noted that FIGS. 2A-2G illustrated formation of an anode layer on the fiber, and formation of a cathode layer on top of the anode layer (e.g., with an electrolyte separation layer separating the cathode and anode layers). In contrast, in FIG. 3D, the cathode layer is first formed on the fabric, and later an anode layer is to be formed on the cathode layer (e.g., with an electrolyte separation layer separating the cathode and anode layers). Deposition of a cathode or an anode layer on the fabric may be a design choice, and in some other embodiments, an anode layer may be deposited in FIG. 3D instead of the cathode layer 310. Deposition of an anode/cathode layer has been discussed in details with respect to FIGS. 2A-2G. In some embodiments, the metal layer 308 may act as a current collector for the cathode layer 310.

Figure 3E:
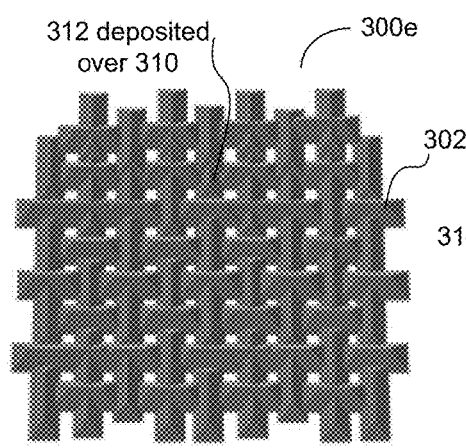

Referring now to FIG. 3E, illustrated is a component 300e comprising the fabric 302, and a separation layer 312 may be deposited on the cathode layer 310. Deposition of a separation layer has been discussed in details with respect to FIG. 2E. In some embodiments, the separation layer 312 may electrically separate the cathode layer 310 from an anode layer that is subsequently formed.

Figure 3F:
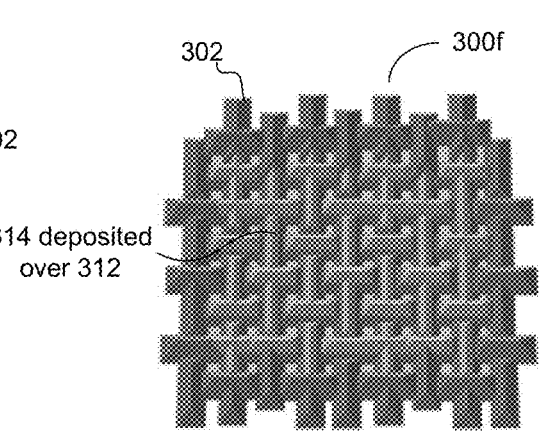

Referring now to FIG. 3F, illustrated is a component 300f comprising the fabric 302, and an anode layer 314 may be deposited on the separation layer 312. In some embodiments, the formation of the anode layer 314 and the cathode layer 310 may be interchanged. Deposition of an anode/cathode layer has been discussed in details with respect to FIGS. 2A-2G.

Figure 3G:
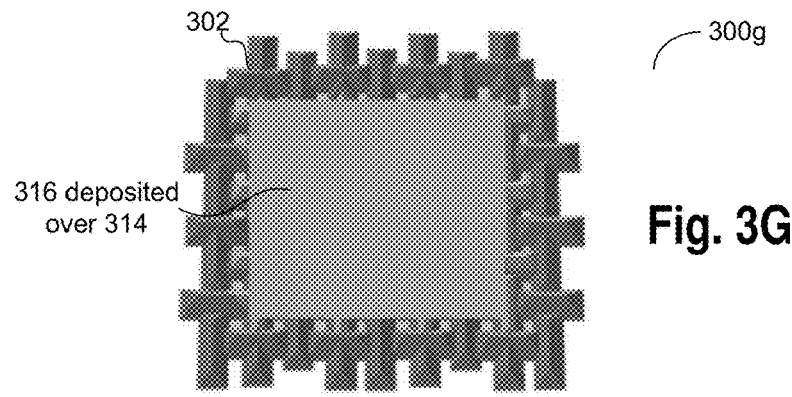

Referring now to FIG. 3G, illustrated is a component 300g comprising the fabric 302, and an anode current collector layer 316 may be deposited on the anode layer 314. In some embodiments, the anode current collector layer 316 may comprise metal, e.g., copper, platinum, gold, nickel, and/or the like. The anode current collector layer 316 may act as a current collector for the anode layer 314. In some embodiments, the anode current collector layer 316 may be a thin and at least partially flexible layer of metal. In some embodiments, the anode current collector layer 316 may be formed by printing a metal layer (e.g., screen printing, ink-jet printing, etc.), by a sputtering operation, by a plating operation, and/or the like.

Figure 3H:
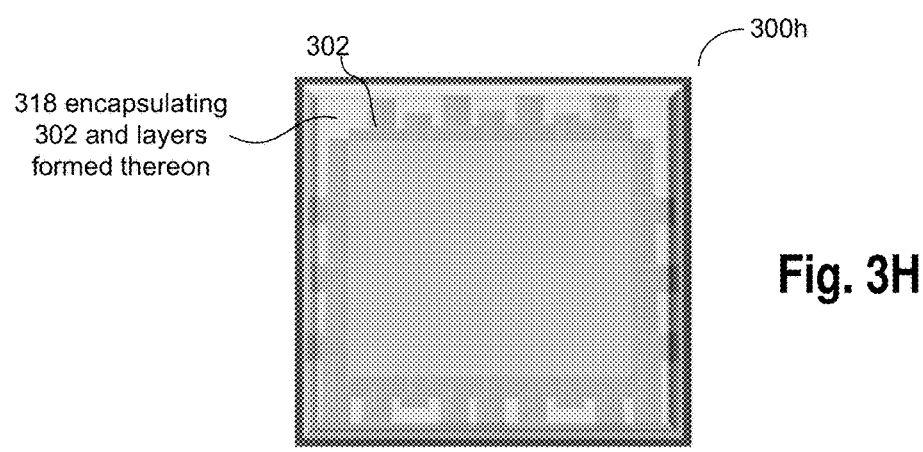

Referring now to FIG. 3H, illustrated is a component 300h comprising the fabric 302, and an encapsulant 318 that may encapsulate the component 300g. For example, the encapsulant 318 may encapsulate the fabric 302 (e.g., at least a section of the fabric 302), after the formation of various layers discussed with respect to FIGS. 3A-3G. In some embodiments, the encapsulant 318 may protect the fabric 302 and the battery formed thereon from degradation. In some embodiments, encapsulant 318 may be formed by laminating one or more sheets of encapsulant, and/or may be formed by a molding process.

Figure 3I:
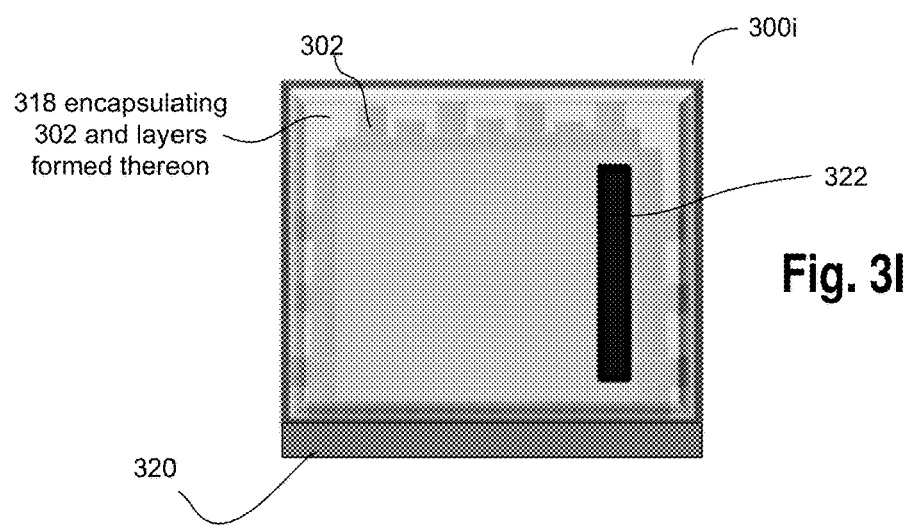

Referring now to FIG. 3I, illustrated is a component 300i comprising the fabric 302, and a cathode contact 320 and an anode contact 322 formed thereon. For example, the encapsulant 318 may be patterned to open up the encapsulant 318 at the locations where the cathode contact 320 and the anode contact 322 are to be formed. Such patterning of the encapsulant 318 may be performed using, for example, skiving, drilling, lithography, wet or dry chemical etching, and/or the like.

For example, a first opening may be formed in the encapsulant 318, where the first opening may expose a section of the metal layer 308, and where the metal layer 308 may act as a current collector layer for the cathode layer 310. Subsequently, the cathode contact 320 (e.g., which may comprise an appropriate type of metal) may be formed in the first opening, such that the cathode contact 320 is attached to the metal layer 308. Similarly, a second opening may be formed in the encapsulant 318, where the second opening exposes at least a section of the anode current collector layer 316. Subsequently, the anode contact 322 (e.g., which may comprise an appropriate type of metal) may be formed in the second opening, such that the anode contact 322 is attached to the anode current collector layer 316. The illustrated location, shape and/or size of the cathode/anode contacts are merely examples, and these contacts can be located at any other location within the component 300i, and/or can have any other appropriate shape and/or size.

Figure 3J:
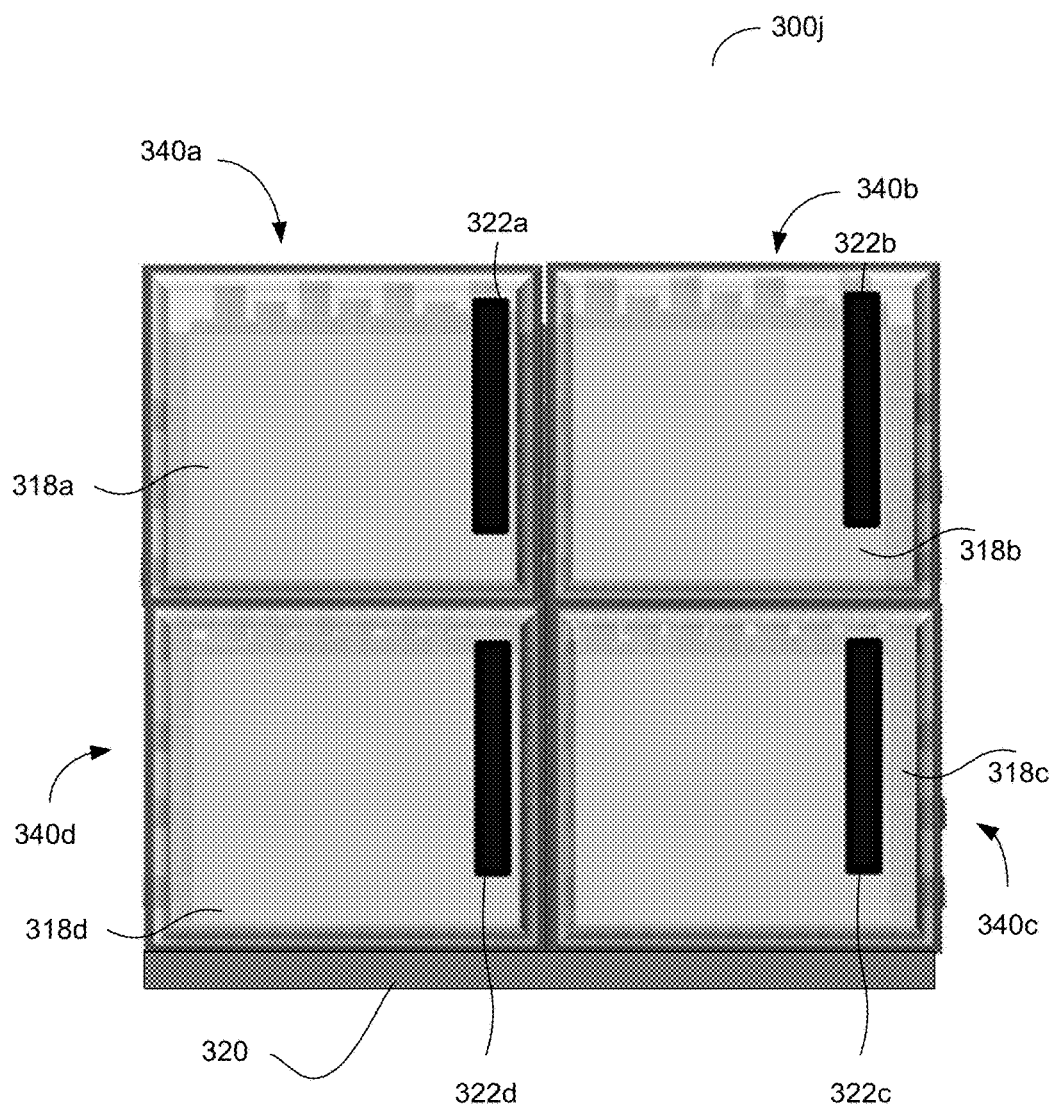

In some embodiments, the component 300i may act as a battery cell that is formed on or embedded in the fabric 302. In some embodiments, more than one such battery cells may be formed on the fabric 302 (e.g., on different sections of the fabric 302), and such battery cells may be interconnected. FIG. 3J illustrates a component 300j that comprises four battery cells 340a, 340b, 340c, and 340d (henceforth also referred to as a battery cell 340 in singular, and battery cells 340 in plural). Each of these battery cells may be similar to the battery cell of the component 300i. For example, the battery cell 340a may comprise an encapsulant 318a and an anode contact 322a formed on a first section of the fabric 302, the battery cell 340b may comprise an encapsulant 318b and an anode contact 322b formed on a second section of the fabric 302, and so on. Various other components of the battery cells 340 (e.g., as discussed with respect to FIGS. 3A-3I) are not illustrated in FIG. 3J, as these components are underneath the respective encapsulant.

In some embodiments, the battery cells 340 may have a common cathode contact 320, although in some other embodiments, the cathode contacts may be separate for the individual battery cells. In some embodiments and although not illustrated in FIG. 3J, the battery cells 340 can have a common anode contact.

Although four battery cells 340a, ..., 340d are illustrated in FIG. 3J, in some embodiments, any other number of battery cells may be formed on the fabric 302. In some embodiments, the fabric 302 may be bendable along the boundaries or edges of the battery cells 340. Thus, for example, if the battery cells 340 are reasonably small in size, the fabric 302 of the component 300j can be flexible, or at least partially flexible (e.g., as the fabric 302 may be bendable along the boundaries of individual battery cells 340a, ..., 340d).

In some embodiments, forming smaller individual battery cells 304a, ..., 304d may increase the flexibility of the fabric 302. In some embodiments, instead of forming four separate battery cells 340a, ..., 340d, one big battery cell may be formed on the fabric 302.

Figure 4:
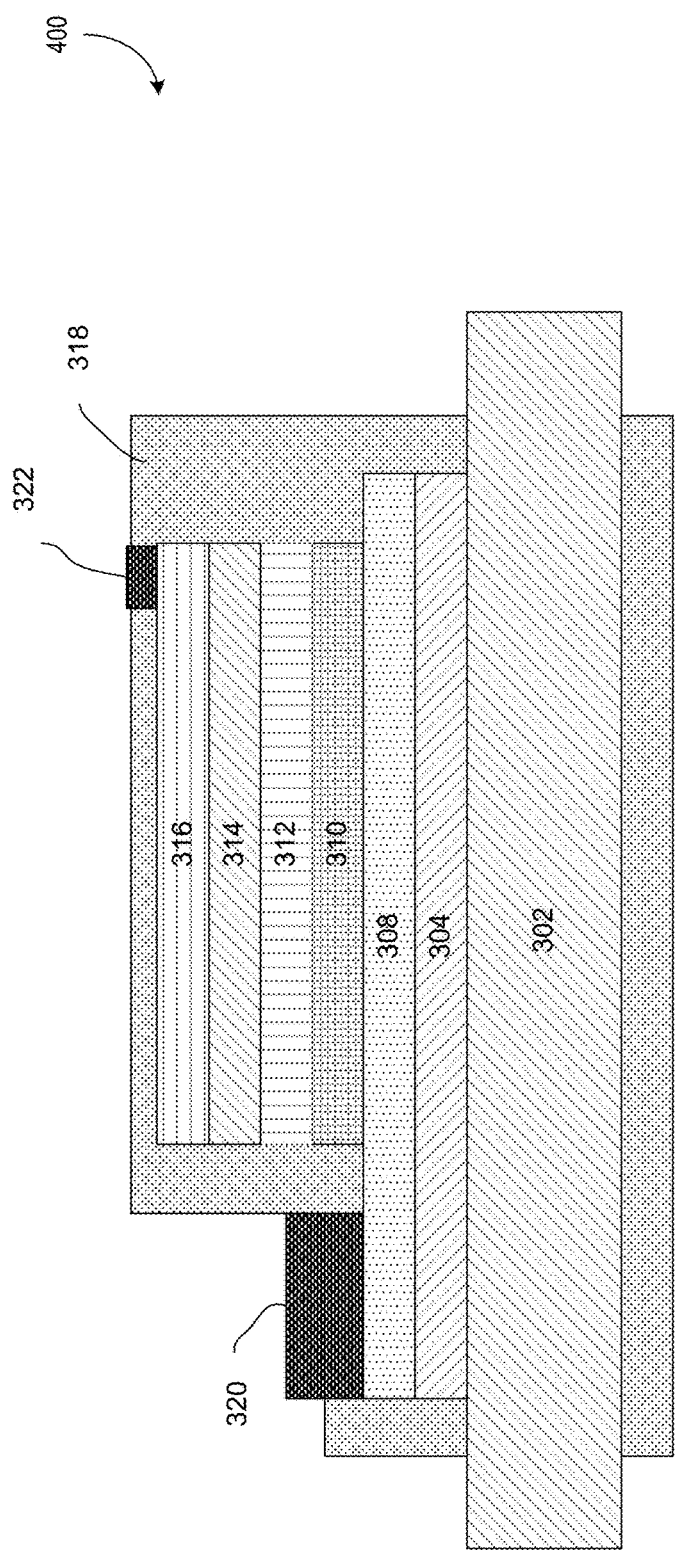
FIG. 4 illustrates a cross sectional view of a battery cell formed on a fabric, according to some embodiments.

FIG. 4 illustrates a cross sectional view of a battery cell 400 formed on the fabric 302, according to some embodiments. The battery cell 400 is similar to the battery cell 300i of FIG. 3I, and various components of FIGS. 3A-3I and FIG. 4 are illustrated using similar labels. For example, the battery cell comprises of fabric 302, the SAM 304 formed on the fabric 302, the metal layer 308 attached to the SAM 304, and the cathode layer 310 formed on the metal layer. In some embodiments, the metal layer 308 may act as a current collector for the cathode layer 308, and the cathode contact 320 may be in contact with the metal layer 308. In some embodiments, the separation layer 312 separates the cathode layer 310 from the anode layer 314. The anode current collector 316 is formed on the anode layer 314. The anode contact 322 may be attached to the anode current collector 316. The encapsulant 318 may encapsulate the battery cell 400. The cathode contact 320 and the anode contact 322 may be formed through respective openings in the encapsulant 318. Various elements of the battery cell 400 are discussed in details with respect to FIGS. 3A-3I, and hence, are not discussed in further details herein.

Figure 5:
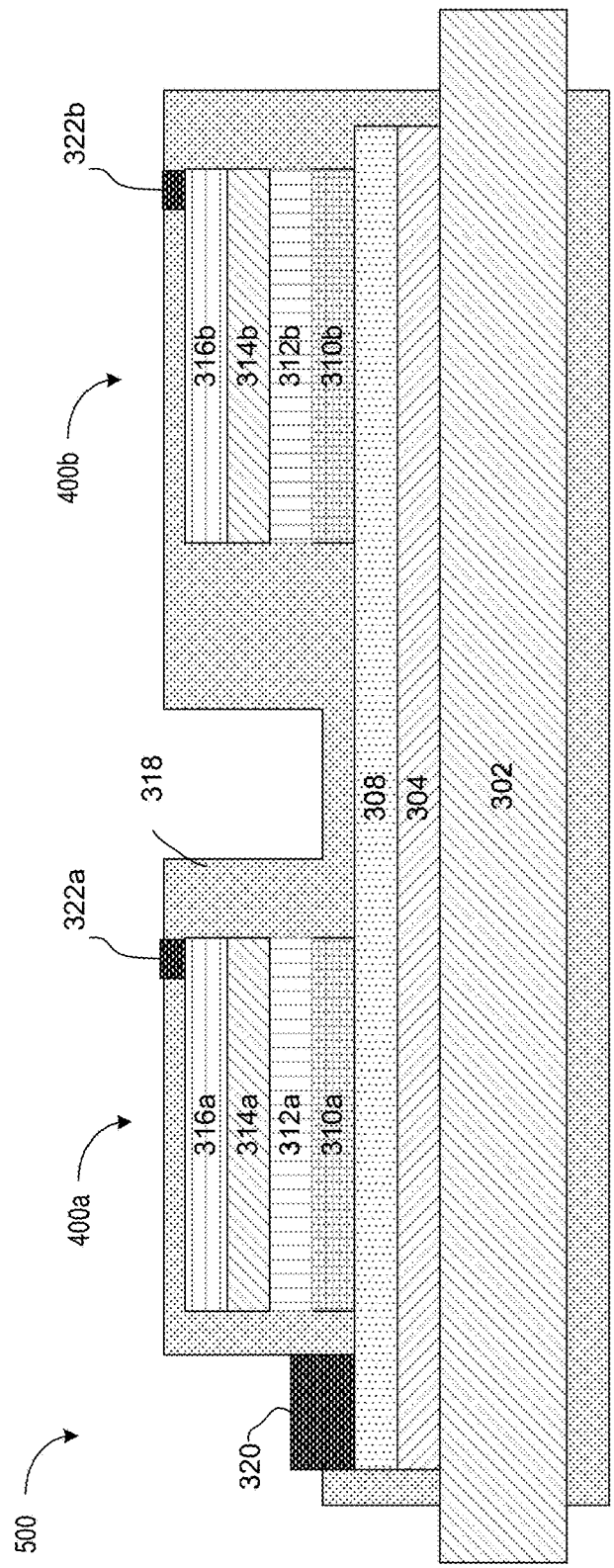
FIG. 5 illustrates a cross sectional view of a component comprising two battery cells formed on a fabric 302 and connected in parallel, according to some embodiments.

FIG. 5 illustrates a cross sectional view of a component 500 comprising two battery cells 400a and 400b formed on the fabric 302 and connected in parallel, according to some embodiments. Each of the battery cells 400a and 400b may be at least in part similar to the battery cell 400 of FIG. 4. For example, similar to FIG. 4, the battery cell 400a may comprise of a SAM 304, a metal layer 308, a cathode layer 310a formed on the metal layer 308, a separation layer 312a, an anode layer 314a, an anode current collector 316a, and an anode contact 322a. The battery cell 400b may also have similar corresponding components.

In some embodiments, the SAM 304 may be common and a continuous layer for both the battery cells 400a and 400b. In some embodiments, the metal layer 308 may be common and a continuous layer for both the battery cells 400a and 400b. As the metal layer 308 may act as a current collector for the cathode layers 310a and 310b of the two battery cells, the cathode layers 310a and 310b of the two battery cells 400a and 400b may be electrically connected through the metal layer 308. In some embodiments, the component 500 may have a single cathode contact 320, which, for example, may act as a common cathode contact for the parallel connected battery cells 400a and 400b.

In some embodiments, the two battery cells 400a and 400b may be encapsulated using a single common encapsulant 318. In some embodiments, to ensure that the two battery cells 400a and 400b are connected in parallel, the anode contacts 322a and 322b may also be connected (e.g., via a connector that runs external to the battery cells 400a and 400b, or runs within the battery cells 400a and 400b but not illustrated in FIG. 5).

Although FIG. 5 illustrates only two battery cells connected in parallel, in some embodiments, more than two battery cells may also be connected in parallel, as would be readily understood by those skilled in the art based on the teachings of this disclosure. Connecting the battery cells in parallel may, for example, increase a current supply capacity of the battery cell combination.

Figure 6:
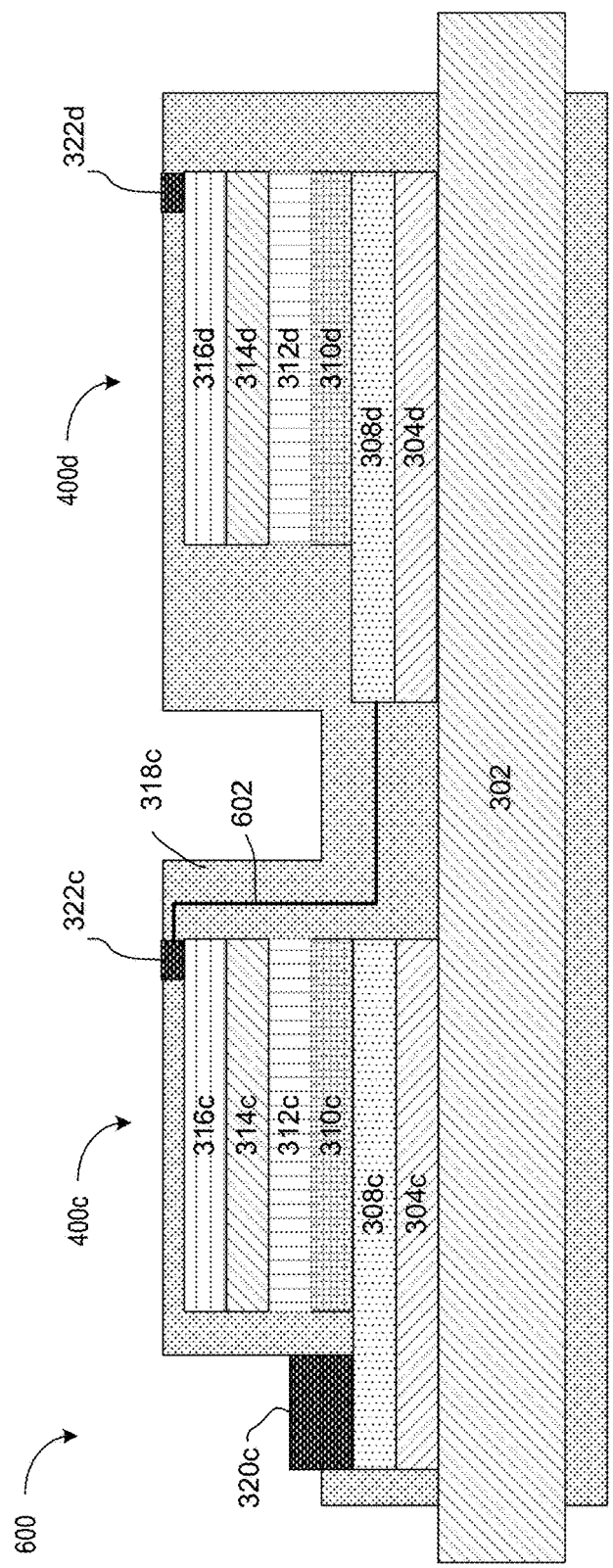
FIG. 6 illustrates a cross sectional view of a component comprising two battery cells formed on a fabric and connected in series, according to some embodiments.

FIG. 6 illustrates a cross sectional view of a component 600 comprising two battery cells 400c and 400d formed on the fabric 302 and connected in series, according to some embodiments. Each of the battery cells 400c and 400d may be at least in part similar to the battery cell 400 of FIG. 4. For example, similar to FIG. 4, the battery cell 400c may comprise a SAM 304c, a metal layer 308c, a cathode layer 310c formed on the metal layer 308c, a cathode contact 320c, a separation layer 312c, an anode layer 314c, an anode current collector 316c, and an anode contact 322c. The battery cell 400d may also have similar corresponding components.

In some embodiments, because the battery cells 400c and 400d are to be connected in series, unlike FIG. 5, in the component 600 of FIG. 6, the two battery cells 400c and 400d may have two separate corresponding metal layers 308c and 308d, respectively (e.g., which may not be connected). Also, the battery cell 400c may include a cathode contact 320c. In some embodiments, the metal layer 308d (e.g., which may be the cathode current collector) may not have a corresponding cathode contact, and the metal layer 308d may be connected to the anode contact 322c, e.g., via a wire or a connection 602. In some embodiments, the anode contact 322c may not (or need not) be accessible from outside the battery cell 400c, although in some other embodiments, the anode contact 322c may be accessible. The cathode contact 320c and the anode contact 322d may form the two accessible contacts for the component 600. In some embodiments, the two battery cells 400c and 400d may be encapsulated using a single common encapsulant 318c.

Although FIG. 6 illustrates only two battery cells 400c and 400d connected in series, in some embodiments, more than two battery cells may also be connected in series, as would be readily understood by those skilled in the art based on the teachings of this disclosure. Connecting the battery cells in series may, for example, increase the voltage supplied by the battery cell combination.

In some embodiments, a configuration of the battery cells (e.g., whether the battery cells are connected in series or parallel, or are standalone cells) may be based on the application for which the section of the fabric 302 in which the battery cells are formed is being used. Merely as an example, the fabric 302 may be worn at least in part on a user's body, e.g., as a part of a smart apparel, textile, or wearable dress developed based on wearable technology. A section of the smart dress may have a sensor (e.g., a sensor to measure a parameter associated with the body, such as temperature, heart rate, etc.). Another section of the dress may have an actuator (e.g., an actuator at or near the wrist of the user, to provide haptic feedback to the user). The sensor may require low voltage and current, while the actuator may require high voltage. Accordingly, the battery cells supplying current to the sensors (and possibly formed on a section of the fabric that is near the sensor) may have a relatively smaller number of series or parallel connected cells. In contrast, the battery cells supplying current to the actuators (and possibly formed on a section of the fabric that is near the actuators) may have a higher number of series or parallel connected cells. In some embodiments, designing distributed battery cells with varying geometric shapes may open up a possibility of creating flexible integrated smart apparel with the necessary energy density to power desired functionalities.

Figure 7:
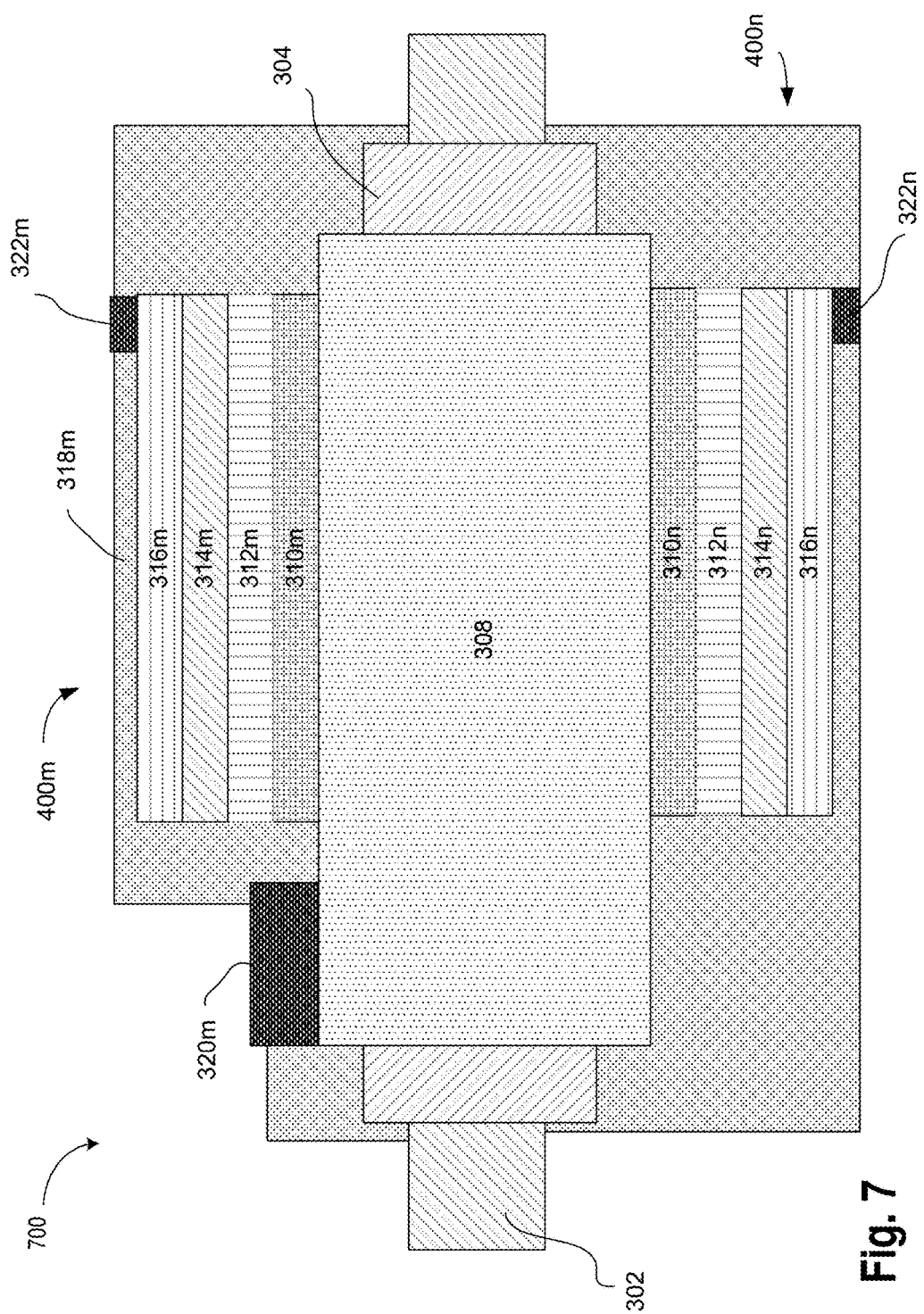
FIG. 7 illustrates a cross sectional view of a component comprising two battery cells formed on two sides of a fabric, according to some embodiments.

FIG. 7 illustrates a cross sectional view of a component 700 comprising two battery cells 400m and 400n formed on two sides of the fabric 302, according to some embodiments. Each of the battery cells 400m and 400n may be at least in part similar to the battery cell 400 of FIG. 4.

In some embodiments, the battery cells 400m and 400n may be formed on both sides of the fabric 302, which is illustrated as a fiber. In the embodiments illustrated in FIG. 7, the battery cells 400m and 400n may be connected in parallel. In some embodiments, the metal layer 308 may be common for both the battery cells 400m and 400n. For example, the SAM 304 may be formed on the periphery of the fiber 302. For example, the SAM 304 may be built directly within the fabric, e.g., by allowing the SAM solution to be selectively deposited and functionalized directly within the individual fibers.

In some embodiments, the metal layer 308 may be formed on the SAM. Thus, the metal layer 308 may be common to both the battery cells 400m and 400n. In some embodiments, as the metal layer 308 is common to both the battery cells 400m and 400n, only one of the battery cells (e.g., the battery cell 400m) may have a cathode contact (e.g., cathode contact 320m of the battery cell 400m).

In some embodiments, at least in part similar to FIG. 4, the battery cell 400m may comprise a cathode layer 310m formed on the metal layer 308, a cathode contact 320m, a separation layer 312m, an anode layer 314m, an anode current collector 316m, and an anode contact 322m. The battery cell 400n similarly has corresponding components. In some embodiments, the two battery cells 400m and 400n may be encapsulated using a single common encapsulant 318m. In some embodiments and although not illustrated, anode contacts 322*m* and 322*n* of the two battery cells 400*m* and 400*n* may be connected via a connection (e.g., if the two battery cells are to be used in parallel), which may be a wire or a connection either within the encapsulant 318*m*, or outside the encapsulant 318*m*.

In some embodiments, any one of at least three voltage levels can be tapped from the component 700, e.g., a first voltage level between the contacts 320*m* and 322*n*, and a second voltage level between the contacts 320*m* and 322*m*, and a third voltage level between the contacts 322*m* and 322*n*.

In some embodiments, forming two battery cells 400*m* and 400*n* on two opposite sides of a fiber or a fabric, for example, may result in improved battery performance, e.g., by the added active surface area available for the battery stack. In an example, the metal layer 308 (e.g., the current collector) may be deposited on each individual fiber in the fabric, and form a 3D platform for desired battery stack. It should be appreciated that different battery stacks and/or different materials may be implemented on each side of the fiber 302. In an example, the battery cell 400*m* may be in parallel or in series with other battery cells, and/or the battery cell 400*n* may be in parallel or in series with other battery cells (or any other appropriate configuration may be possible).

Various embodiments discussed herein is associated with one or more battery cells being formed on fibers or a fabric. In some embodiments, in accordance with the various embodiments discussed in this disclosure, one or more battery cells may be formed on a material that is commonly used with textiles, such as polyurethane sheets (e.g., TPU). In some embodiments, polyurethane sheets or TPUs may be used to provide waterproofing for fabrics and then bonded to the textile. In an example, once the battery cells are formed on polyurethane sheets, the polyurethane sheets (with the batteries formed thereon) may be attached to another fabric, another apparel, etc. For example, the polyurethane sheets may be laminated onto the fabric or apparel, and/or may be bonded to the fabric or apparel via temperature activated adhesive. The polyurethane sheets may provide various functionalities to the fabric or apparel, e.g., provide waterproofing to the fabric or apparel. Although polyurethane sheets or TPU are used as mere examples, in some embodiments, battery cells may be formed on any appropriate type of material, and subsequently, such material may be attached, bonded, and/or laminated to an appropriate fabric or apparel.

Figure 8:
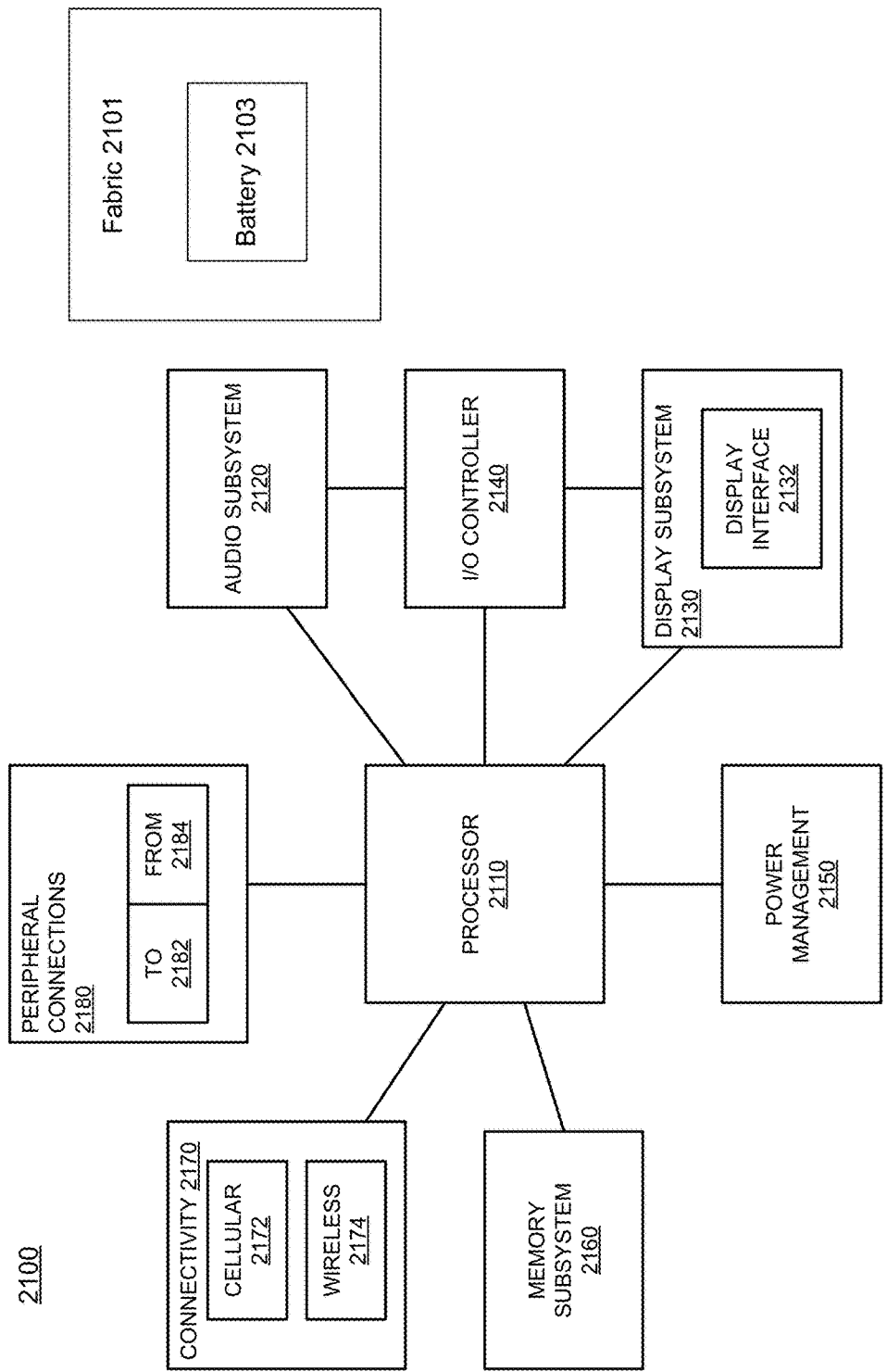
FIG. 8 illustrates a computer system or a SoC (System-on-Chip), where a battery may be formed on a fabric associated with the computing system, in accordance with some embodiments.

FIG. 8 illustrates a computer system or a SoC (System-on-Chip) 2100, where a battery may be formed on a fabric associated with the computing system 2100, in accordance with some embodiments. It is pointed out that those elements of FIG. 8 having the same reference numbers (or names) as the elements of any other figure can operate or function in any manner similar to that described, but are not limited to such.

In some embodiments, computing device 2100 represents an appropriate computing device, such as a computing tablet, a mobile phone or smart-phone, a laptop, a desktop, an IOT device, a server, a set-top box, a wireless-enabled e-reader, or the like. It will be understood that certain components are shown generally, and not all components of such a device are shown in computing device 2100.

In some embodiments, computing device 2100 includes a first processor 2110. The various embodiments of the present disclosure may also comprise a network interface within 2100 such as a wireless interface so that a system embodiment may be incorporated into a wireless device, for example, such as a cell phone or personal digital assistant.

In one embodiment, processor 2110 can include one or more physical devices, such as microprocessors, application processors, microcontrollers, programmable logic devices, or other processing means. The processing operations performed by processor 2110 include the execution of an operating platform or operating system on which applications and/or device functions are executed. The processing operations include operations related to I/O (input/output) with a human user or with other devices, operations related to power management, and/or operations related to connecting the computing device 2100 to another device. The processing operations may also include operations related to audio I/O and/or display I/O.

In one embodiment, computing device 2100 includes audio subsystem 2120, which represents hardware (e.g., audio hardware and audio circuits) and software (e.g., drivers, codecs) components associated with providing audio functions to the computing device. Audio functions can include speaker and/or headphone output, as well as microphone input. Devices for such functions can be integrated into computing device 2100, or connected to the computing device 2100. In one embodiment, a user interacts with the computing device 2100 by providing audio commands that are received and processed by processor 2110.

Display subsystem 2130 represents hardware (e.g., display devices) and software (e.g., drivers) components that provide a visual and/or tactile display for a user to interact with the computing device 2100. Display subsystem 2130 includes display interface 2132, which includes the particular screen or hardware device used to provide a display to a user. In one embodiment, display interface 2132 includes logic separate from processor 2110 to perform at least some processing related to the display. In one embodiment, display subsystem 2130 includes a touch screen (or touch pad) device that provides both output and input to a user.

I/O controller 2140 represents hardware devices and software components related to interaction with a user. I/O controller 2140 is operable to manage hardware that is part of audio subsystem 2120 and/or display subsystem 2130. Additionally, I/O controller 2140 illustrates a connection point for additional devices that connect to computing device 2100 through which a user might interact with the system. For example, devices that can be attached to the computing device 2100 might include microphone devices, speaker or stereo systems, video systems or other display devices, keyboard or keypad devices, or other I/O devices for use with specific applications such as card readers or other devices.

As mentioned above, I/O controller 2140 can interact with audio subsystem 2120 and/or display subsystem 2130. For example, input through a microphone or other audio device can provide input or commands for one or more applications or functions of the computing device 2100. Additionally, audio output can be provided instead of, or in addition to display output. In another example, if display subsystem 2130 includes a touch screen, the display device also acts as an input device, which can be at least partially managed by I/O controller 2140. There can also be additional buttons or switches on the computing device 2100 to provide I/O functions managed by I/O controller 2140.

In one embodiment, I/O controller 2140 manages devices such as accelerometers, cameras, light sensors or other environmental sensors, or other hardware that can be included in the computing device 2100. The input can be part of direct user interaction, as well as providing environmental input to the system to influence its operations (such as filtering for noise, adjusting displays for brightness detection, applying a flash for a camera, or other features).

In one embodiment, computing device 2100 includes power management 2150 that manages battery power usage, charging of the battery, and features related to power saving operation. Memory subsystem 2160 includes memory devices for storing information in computing device 2100. Memory can include nonvolatile (state does not change if power to the memory device is interrupted) and/or volatile (state is indeterminate if power to the memory device is interrupted) memory devices. Memory subsystem 2160 can store application data, user data, music, photos, documents, or other data, as well as system data (whether long-term or temporary) related to the execution of the applications and functions of the computing device 2100.

Elements of embodiments are also provided as a machine-readable medium (e.g., memory 2160) for storing the computer-executable instructions (e.g., instructions to implement any other processes discussed herein). The machine-readable medium (e.g., memory 2160) may include, but is not limited to, flash memory, optical disks, CD-ROMs, DVD ROMs, RAMs, EPROMs, EEPROMs, magnetic or optical cards, phase change memory (PCM), or other types of machine-readable media suitable for storing electronic or computer-executable instructions. For example, embodiments of the disclosure may be downloaded as a computer program (e.g., BIOS) which may be transferred from a remote computer (e.g., a server) to a requesting computer (e.g., a client) by way of data signals via a communication link (e.g., a modem or network connection).

Connectivity 2170 includes hardware devices (e.g., wireless and/or wired connectors and communication hardware) and software components (e.g., drivers, protocol stacks) to enable the computing device 2100 to communicate with external devices. The computing device 2100 could be separate devices, such as other computing devices, wireless access points or base stations, as well as peripherals such as headsets, printers, or other devices.

Connectivity 2170 can include multiple different types of connectivity. To generalize, the computing device 2100 is illustrated with cellular connectivity 2172 and wireless connectivity 2174. Cellular connectivity 2172 refers generally to cellular network connectivity provided by wireless carriers, such as provided via GSM (global system for mobile communications) or variations or derivatives, CDMA (code division multiple access) or variations or derivatives, TDM (time division multiplexing) or variations or derivatives, or other cellular service standards. Wireless connectivity (or wireless interface) 2174 refers to wireless connectivity that is not cellular, and can include personal area networks (such as Bluetooth, Near Field, etc.), local area networks (such as Wi-Fi), and/or wide area networks (such as WiMax), or other wireless communication.

Peripheral connections 2180 include hardware interfaces and connectors, as well as software components (e.g., drivers, protocol stacks) to make peripheral connections. It will be understood that the computing device 2100 could both be a peripheral device ("to" 2182) to other computing devices, as well as have peripheral devices ("from" 2184) connected to it. The computing device 2100 commonly has a "docking" connector to connect to other computing devices for purposes such as managing (e.g., downloading and/or uploading, changing, synchronizing) content on computing device 2100. Additionally, a docking connector can allow computing device 2100 to connect to certain peripherals that allow the computing device 2100 to control content output, for example, to audiovisual or other systems.

In addition to a proprietary docking connector or other proprietary connection hardware, the computing device 2100 can make peripheral connections 2180 via common or standards-based connectors. Common types can include a Universal Serial Bus (USB) connector (which can include any of a number of different hardware interfaces), DisplayPort including MiniDisplayPort (MDP), High Definition Multimedia Interface (HDMI), Firewire, or other types.

In some embodiments, the computing device 2100 may be a smart apparel, a smart fabric, a smart dress in accordance with wearable technology, and/or the like. For example, various components of the computing device 2100 (e.g., a processor, a memory, and/or the like) may be formed or embedded within the smart apparel. Furthermore, in some embodiments, the smart apparel may include at least a section of a fabric 2101, and a battery 2103 (or a stack of battery cells) may be formed on the section of the fabric 2101, e.g., as discussed with respect to FIGS. 1A-7.

Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. If the specification states a component, feature, structure, or characteristic "may," "might," or "could" be included, that particular component, feature, structure, or characteristic is not required to be included. If the specification or claim refers to "a" or "an" element, that does not mean there is only one of the elements. If the specification or claims refer to "an additional" element, that does not preclude there being more than one of the additional element.

Furthermore, the particular features, structures, functions, or characteristics may be combined in any suitable manner in one or more embodiments. For example, a first embodiment may be combined with a second embodiment anywhere the particular features, structures, functions, or characteristics associated with the two embodiments are not mutually exclusive While the disclosure has been described in conjunction with specific embodiments thereof, many alternatives, modifications and variations of such embodiments will be apparent to those of ordinary skill in the art in light of the foregoing description. The embodiments of the disclosure are intended to embrace all such alternatives, modifications, and variations as to fall within the broad scope of the appended claims.

In addition, well known power/ground connections to integrated circuit (IC) chips and other components may or may not be shown within the presented figures, for simplicity of illustration and discussion, and so as not to obscure the disclosure. Further, arrangements may be shown in block diagram form in order to avoid obscuring the disclosure, and also in view of the fact that specifics with respect to implementation of such block diagram arrangements are highly dependent upon the platform within which the present disclosure is to be implemented (i.e., such specifics should be well within purview of one skilled in the art). Where specific details (e.g., circuits) are set forth in order to describe example embodiments of the disclosure, it should be apparent to one skilled in the art that the disclosure can be practiced without, or with variation of, these specific details. The description is thus to be regarded as illustrative instead of limiting.

The following example clauses pertain to further embodiments. Specifics in the example clauses may be used anywhere in one or more embodiments. All optional features of the apparatus described herein may also be implemented with respect to a method or process.

Clause 1. An apparatus comprising: a fabric; a layer formed on the fabric; and a battery cell formed on the fabric, wherein a current collector of the battery cell is at least in part formed on the layer.

Clause 2. The apparatus of claim 1, wherein the layer comprises self-assembled monolayer (SAM) material.

Clause 3. The apparatus of any of claim 1 or 2, wherein the layer has a thickness between about 0.5 nanometer (nm) to about 2.5 nm.

Clause 4. The apparatus of any of claims 1-3, wherein the layer comprises one of amine group (—NH2), thiol (—SH), carboxylic acid (—COOH), or Pyridyl.

Clause 5. The apparatus of any of claims 1-4, further comprising: a cathode layer of the battery cell formed on the fabric and stacked on the current collector; and an anode layer of the battery cell formed on the fabric and stacked on the cathode layer.

Clause 6. The apparatus of claim 5, further comprising: a separation layer of the battery cell formed on the fabric and stacked between the anode layer and the cathode layer.

Clause 7. The apparatus of any of claims 1-6, wherein the current collector comprises a metal layer deposited on the layer.

Clause 8. The apparatus of any of claims 1-7, wherein: the fabric comprises functional group molecules; and the layer is formed on the fabric by utilizing the functional group molecules as active sites and anchor points for molecules of the layer to chemically adhere to.

Clause 9. The apparatus of any of claims 1-8, wherein the battery cell is a first battery cell, wherein the battery cell is formed on a first surface of a first side of the fabric, and wherein the apparatus further comprises: a second battery cell formed on a second surface of a second side of the fabric.

Clause 10. The apparatus of claim 9, wherein current collector of the first battery cell is a first current collector, wherein the second battery cell comprises: a second current collector formed on the SAM material formed on the second surface of the second side of the fabric.

Clause 11. The apparatus of any of claims 1-8, wherein the battery cell is a first battery cell, wherein the battery cell is formed on a section of the fabric, and wherein the apparatus further comprises: a second battery cell formed on a second section of the fabric.

Clause 12. The apparatus of claim 11, wherein the first and second battery cells comprise: the current collector that is common to both the first battery cell and the second battery cell.

Clause 13. The apparatus of claim 11, wherein the first battery cell and the second battery cell are connected in one of a parallel configuration or a series configuration.

Clause 14. The apparatus of any of claims 1-13, wherein the apparatus comprises a smart wearable apparel to measure a body parameter and/or to provide actuation.

Clause 15. A system comprising: a processor; a memory coupled to the processor; a battery to supply power to one or both the processor or the memory; and a fabric, wherein the battery is formed on the fabric.

Clause 16. The system of claim 15, wherein the battery comprises: a current collector comprising a metal layer, wherein the current collector is attached to the fabric using a layer of self-assembled monolayer (SAM) material.

Clause 17. The system of any of claims 15-16, further comprising: an array of batteries formed on the fabric, wherein the fabric is bendable along boundaries of individual battery cells of the array of batteries.

Clause 18. The system of any of claims 15-17, further comprising: a wireless interface to wirelessly communicate with an external system.

Clause 19. A method comprising: forming a self-assembled monolayer (SAM) on a fiber; forming a layer of catalyst on the SAM; and forming a metal layer on the SAM, the formation of the metal layer being facilitated by the layer of catalyst.

Clause 20. The method of claim 19, wherein the metal layer is a first metal layer, and wherein the method further comprises: forming an anode layer and a cathode layer on the first metal layer, the first metal layer to act as a current collector for one of the anode layer and the cathode layer; forming a second metal layer, the second metal layer to act as a current collector for another of the anode layer and the cathode layer; forming a separation layer that separates the anode layer and the cathode layer; and forming a battery cell, the battery cell comprising the anode layer, the cathode layer, the first metal layer, and the second metal layer.

Clause 21. The method of any of claims 19-20, further comprising: producing a wearable smart apparel from the fiber, with the battery cell being formed on the fiber.

Clause 22. An apparatus comprising: a material; a battery cell formed on the material; and a fabric, wherein the material, with the battery cell formed thereon, is attached to the fabric.

Clause 23. The apparatus of claim 22, wherein: the material, with the battery cell formed thereon, is laminated onto the fabric; and the material is one of polyurethane sheets or thermoplastic polyurethane (TPU).

Clause 24. The apparatus of any of claims 22-23, further comprising: self-assembled monolayer (SAM) formed on the material, wherein the battery cell is formed on the SAM, and wherein the material is bonded to the fabric via temperature activated adhesive.

Clause 25. The apparatus of any of claims 22-24, wherein the apparatus comprises a smart wearable apparel to measure a body parameter and/or to provide actuation.

Clause 26. An apparatus comprising: means for forming a self-assembled monolayer (SAM) on a fiber; means for forming a layer of catalyst on the SAM; and means for forming a metal layer on the SAM, the means for forming the metal layer being facilitated by the layer of catalyst.

Clause 27. The apparatus of claim 26, wherein the metal layer is a first metal layer, and wherein the apparatus further comprises: means for forming an anode layer and a cathode layer on the first metal layer, the first metal layer to act as a current collector for one of the anode layer and the cathode layer; means for forming a second metal layer, the second metal layer to act as a current collector for another of the anode layer and the cathode layer; means for forming a separation layer that separates the anode layer and the cathode layer; and means for forming a battery cell, the battery cell comprising the anode layer, the cathode layer, the first metal layer, and the second metal layer.

Clause 28. The apparatus of any of claims 26-27, further comprising: means for producing a wearable smart apparel from the fiber, with the battery cell being formed on the fiber.

An abstract is provided that will allow the reader to ascertain the nature and gist of the technical disclosure. The abstract is submitted with the understanding that it will not be used to limit the scope or meaning of the claims. The following claims are hereby incorporated into the detailed description, with each claim standing on its own as a separate embodiment.

We claim:

1. An apparatus comprising:
   a fabric;
   a layer on the fabric, wherein the layer comprises self-assembled monolayer (SAM) material; and
   a battery cell on the fabric, wherein the battery cell comprises a current collector on the layer.

2. The apparatus of claim 1, wherein the layer has a thickness between about 0.5 nanometer (nm) to about 2.5 nm.

3. The apparatus of claim 1, further comprising:
   a cathode layer of the battery cell on the fabric and stacked on the current collector; and
   an anode layer of the battery cell on the fabric and stacked on the cathode layer.

4. The apparatus of claim 3, wherein the battery cell further comprises:
   a separation layer between the anode layer and the cathode layer.

5. The apparatus of claim 1, wherein the current collector comprises metal.

6. The apparatus of claim 1, wherein:
   the fabric comprises functional group molecules; and
   the layer on the fabric applies functional group molecules as active sites and anchor points for molecules of the layer to chemically adhere to.

7. The apparatus of claim 1, wherein the battery cell is a first battery cell, wherein the battery cell is on a first surface of a first side of the fabric, and wherein the apparatus further comprises:
   a second battery cell on a second surface of a second side of the fabric.

8. The apparatus of claim 7, wherein the current collector of the first battery cell is a first current collector, wherein the second battery cell comprises:
   a second current collector on the second surface of the second side of the fabric.

9. The apparatus of claim 1, wherein the battery cell is a first battery cell, wherein the battery cell is on a first section of the fabric, and wherein the apparatus further comprises:
   a second battery cell on a second section of the fabric.

10. The apparatus of claim 9, wherein the first and second battery cells comprise:
    the current collector that is common to both the first battery cell and the second battery cell.

11. The apparatus of claim 9, wherein the first battery cell and the second battery cell are coupled in one of a parallel configuration or a series configuration.

12. The apparatus of claim 1, wherein the apparatus comprises a wearable apparel to measure a body parameter and/or to provide actuation.

13. An apparatus comprising:
    a fabric;
    a layer on the fabric; and
    a battery cell on the fabric, wherein a current collector of the battery cell is at least in part on the layer,
    wherein the layer comprises at least one of: amine group (—NH2), thiol (—SH), carboxylic acid (—COOH), or Pyridyl.

14. An apparatus comprising:
    a fabric;
    a layer on the fabric; and
    a battery cell on the fabric,
    wherein a current collector of the battery cell is at least in part on the layer,
    wherein the fabric comprises functional group molecules; and
    wherein the layer on the fabric applies the functional group molecules as active sites and anchor points for molecules of the layer to chemically adhere to.

15. The apparatus of claim 14, wherein the layer comprises monolayer material.

16. The apparatus of claim 14, wherein the layer comprises self-assembled monolayer (SAM) material.

17. The apparatus of claim 14, wherein the battery cell further comprises:
    a separation layer between an anode layer and a cathode layer, wherein the separation layer encircle at least a section of one or more fibers of the fabric.

18. The apparatus of claim 17, wherein the current collector is a first current collector, and wherein the battery cell further comprises:
    a second current collector on the cathode layer and an anode layer, wherein the second current collector encircles at least the section of one or more fibers of the fabric.

19. The apparatus of claim 14, wherein the apparatus comprises a wearable apparel.

20. An apparatus comprising:
    a material;
    a battery cell on the material; and
    a fabric, wherein the material, with the battery cell thereon, is attached to the fabric,
    wherein the material, with the battery cell thereon, is laminated onto the fabric; and
    wherein the material is one of polyurethane sheets or thermoplastic polyurethane (TPU).

21. The apparatus of claim 20, further comprising:
    self-assembled monolayer (SAM) on the material,
    wherein the battery cell is on the SAM, and
    wherein the material is bonded to the fabric via temperature activated adhesive.

22. An apparatus comprising:
    a fabric comprising a plurality of fibers;
    a layer on one or more fibers of the plurality of fibers of the fabric, wherein the layer comprises at least one of: amine group (—NH2), thiol (—SH), carboxylic acid (—COOH), or Pyridyl; and
    a battery cell on the fabric, wherein the battery cell comprises:
      a current collector on the layer,
      a cathode layer and an anode layer on the current collector, wherein the cathode layer and the anode layer encircle at least a section of the one or more fibers.

23. The apparatus of claim 22, wherein the layer comprises monolayer material.

* * * * *